United States Patent
Leuthold et al.

(10) Patent No.: US 12,252,680 B2
(45) Date of Patent: Mar. 18, 2025

(54) BIOREACTOR WITH FILTER UNIT AND METHOD FOR TREATING A CELL BROTH

(71) Applicant: Sartorius Stedim Biotech GmbH, Goettingen (DE)

(72) Inventors: Martin Leuthold, Goettingen (DE); Alexander Helling, Ebergoetzen (DE); Ulrich Grummert, Bad Sooden-Allendorf (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 534 days.

(21) Appl. No.: 17/168,556

(22) Filed: Feb. 5, 2021

(65) Prior Publication Data
US 2021/0155888 A1    May 27, 2021

Related U.S. Application Data (63) Continuation of application No. PCT/EP2019/071199, filed on Aug. 7, 2019.

(30) Foreign Application Priority Data

Aug. 8, 2018 (DE) ...................... 10 2018 006 286.5

(51) Int. Cl.
*C12M 1/00* (2006.01)
*B01D 61/14* (2006.01)

(52) U.S. Cl.
CPC ........... *C12M 29/04* (2013.01); *B01D 61/147* (2013.01); *C12M 29/10* (2013.01); *C12M 47/10* (2013.01); *B01D 2319/025* (2013.01)

(58) Field of Classification Search
CPC ...... C12M 29/04; C12M 29/10; C12M 47/10; B01D 61/147; B01D 2319/025
(Continued)

(56) References Cited

U.S. PATENT DOCUMENTS 5,503,750 A    4/1996    Russo, Jr. et al.
9,090,910 B2 *  7/2015    Mehta .................... C12N 13/00
(Continued)

FOREIGN PATENT DOCUMENTS

CA    2993709 A1 *  2/2017  ............ C12M 23/28
DE    10022259 A1    11/2001
(Continued)

OTHER PUBLICATIONS

International Search Report, PCT/EP2019/071199, Nov. 7, 2019, 4 pages.
(Continued)

*Primary Examiner* — Michael L Hobbs
*Assistant Examiner* — Lenora A Abel
(74) *Attorney, Agent, or Firm* — Edell, Shapiro & Finnan, LLC (57) ABSTRACT

A bioreactor having a filter unit and a method for treating a cell broth. The filter unit has a supply channel (2), a first filter medium (4), a retentate channel (1), a second filter medium (5) and a permeate channel (3), arranged so that the first filter medium delimits the supply channel and the retentate channel from one another; and the second filter medium delimits the retentate channel and the permeate channel from one another. The supply channel is connected to an inlet for a supply medium; the retentate channel is connected to an inlet for a cell broth and to an outlet for the cell broth; the permeate channel is connected to an outlet for a permeate; and the interior of the bioreactor is connected to the inlet for the cell broth and to the outlet for the cell broth.

12 Claims, 6 Drawing Sheets

(58) Field of Classification Search
USPC .................................................... 435/289.1
See application file for complete search history.

(56) References Cited

U.S. PATENT DOCUMENTS

| | | | |
|---|---|---|---|
| 11,931,733 B2 * | 3/2024 | Leuthold | B01D 61/146 |
| 2003/0173285 A1 | 9/2003 | Schmidt et al. | |
| 2008/0237110 A1 | 10/2008 | Lightfoot et al. | |
| 2019/0030486 A1 | 1/2019 | Leuthold et al. | |
| 2020/0139303 A1 * | 5/2020 | Dupont | B01D 63/082 |

FOREIGN PATENT DOCUMENTS

| | | |
|---|---|---|
| DE | 102016004115 A1 | 10/2017 |
| EP | 2441826 A1 | 4/2012 |
| WO | 2005113119 A1 | 12/2005 |
| WO | 2017143065 A1 | 8/2017 |
| WO | 2017174192 A1 | 10/2017 |

OTHER PUBLICATIONS

Davila "Characterization of Ultra and Nanofiltration Commercial Filters by Liquid-Liquid Displacement Porosimetry", (2013), 133 pages.

Shrestha "Characterization of Porous Membranes Via Porometry", (2012), 103 pages.

Reingruber et al., "Quantitative characterization of microfiltration membranes by 3D reconstruction", Journal of Membrane Science, 372 (2011) 66-74, also in Fuel and Energy Abstracts Apr. 2011, 10 pages.

* cited by examiner

BIOREACTOR WITH FILTER UNIT AND METHOD FOR TREATING A CELL BROTH

CROSS REFERENCE TO RELATED APPLICATIONS

This is a Continuation of International Application PCT/EP2019/071199 which has an international filing date of Aug. 7, 2019, and the disclosure of which is incorporated in its entirety into the present Continuation by reference. This Continuation also claims foreign priority under 35 U.S.C. § 119(a)-(d) to and also incorporates by reference, in its entirety, German Patent Application 10 2018 006 286.5 filed on Aug. 8, 2018.

FIELD OF INVENTION

The present invention relates to a bioreactor with a filter unit and to a method for treating a cell broth.

BACKGROUND

The treatment of cell broths is of central importance in biochemical processes, in which biological cells are used. Most of the aforesaid processes have, in particular, one or more steps of washing, concentrating, isolating and fractionating.

In said processes, for example, conventional techniques, such as centrifuging, alternating tangential flow filtration (ATF) and sedimentation are used. These processes have a drawback that they do not allow any direct supply of fluids (for example, fresh supply medium) to the cell broth during the separation step (filtration and/or sedimentation); and, as a result, two separate process steps have to be carried out. In addition, the apparatuses, required for these processes, take up a large amount of space (negligible compactness); and the processes are associated with a considerable amount of time and effort. Moreover, in some of the known methods, the cells are subjected to a considerable load.

SUMMARY

Therefore, objects of the present invention include providing a method, which is suitable for treating a cell broth, which is suitable for a continuous processing mode and which is suited to preserve the cells contained in the broth. Further, associated objects include providing a bioreactor, which is suitable for carrying out said method.

The above objects are addressed with the embodiments characterized in the claims.

In a first aspect, the present invention relates to a bioreactor with a filter unit, wherein the bioreactor has an interior; and the filter unit comprises at least one supply channel, at least one first filter medium, at least one retentate channel, at least one second filter medium and at least one permeate channel, arranged in such a way that the first filter medium delimits the supply channel and the retentate channel from one another; and the second filter medium delimits the retentate channel and the permeate channel from one another, wherein the supply channel is connected in a fluid conducting manner to at least one inlet for a supply medium; the retentate channel is connected in a fluid conducting manner to at least one inlet for a cell broth and to at least one outlet for the cell broth; the permeate channel is connected in a fluid conducting manner to at least one outlet for a permeate; and the interior of the reactor is connected in a fluid conducting manner to the inlet for the cell broth and to the outlet for the cell broth.

Both cell broth and supply medium can be added continuously to the filter unit of the bioreactor of the present invention, so that the bioreactor can be operated continuously. As a result, the bioreactor of the present invention enables an efficient and economical processing. The invention leads, in particular, to a reduction in the processing times and the amount of equipment required. In addition, dead zones (i.e., regions, in which a portion of the cell broth sediments over a prolonged period of time) are avoided, while at the same time the cells are treated gently. In addition, the bioreactor of the present invention permits the integration of several steps (for example, supply of fresh supply medium and isolation of products from the cell broth and/or isolation of a portion of the cells (fractionation of the cells)) into a single step.

In general, a cell broth is understood to mean a mixture that contains
- water or a culture medium and
- (biological) cells and, optionally, their decomposition products (for example cell fragments) as well as
- optionally, metabolic products of the cells.

A cell broth can contain, for example, cells as well as a culture medium, proteins, nucleotides, metabolic products of the cells and/or decomposition products of the cells. In accordance with an aspect of the present invention, the cell broth contains preferably a culture medium.

"Cells" include, according to the present invention, those that humans, animals, plants, fungi, algae and bacteria have as their origin, and also viruses.

The culture medium is generally referred to as a nutrient medium that is used for cultivating cells. The culture medium is preferably an aqueous culture medium.

A fluid is understood to mean, according to the present invention, a liquid or gaseous mixture or a liquid or gaseous compound. For example, a washing buffer represents a fluid. A culture medium or its liquid or gaseous components can also be a fluid.

A "bioreactor" is understood to mean, according to the present invention, a reactor, in the interior of which a cell broth can be cultivated. In accordance with an aspect of the invention, the interior can be closed, wherein "closed" in this context means that no free substance exchange with the environment takes place. However, the interior of the bioreactor can also be open. The interior is preferably closed.

In accordance with a preferred embodiment, the filter unit is a flat filter module, spiral wound fiber module or hollow fiber module, where in this case a flat filter module is preferred. If the filter unit is designed as a flat filter module, then the first filter medium and the second filter medium have a flat shape. The term "flat" indicates that the respective filter medium (filter material) lies substantially in a single plane. Preferably all filter media lie substantially in planes that are largely parallel to one another. The filter media which are suitable according to the present invention are not subject to any particular restriction and can be, for example, ceramic membranes, nonwovens and polymer membranes.

In accordance with an aspect of the present invention, the filter unit can be arranged inside or outside the interior. In accordance with a preferred embodiment, the filter unit is arranged inside the interior of the bioreactor. In such an arrangement the dead volume decreases as a result of the short paths between the filter unit and the interior of the bioreactor, so that the residence time of the cells outside the interior is short. In addition, an arrangement inside the interior does not require any additional/separate measures, for example for controlling the temperature of the cell broth or of the supplied supply medium or the like. Another advantage of this arrangement is that the space requirement is reduced.

In the case of an arrangement of the filter unit in the interior of the bioreactor, the bioreactor has preferably an outer connection for the supply medium. Supply medium can be supplied to the supply channel from the outside by way of the connection.

In accordance with a particularly preferred embodiment, the filter unit is arranged outside the bioreactor. A bioreactor having this construction is simpler and faster to produce, so that a wide variety of possible uses are available with a high degree of flexibility. This arrangement is also particularly suitable for repeated use (reuse). An additional advantage is the fact that a bioreactor having this arrangement has a design with a low level of complexity.

In accordance with another of the preferred embodiments of the present invention, the inlet for the supply medium is connected in a fluid conducting manner to a pump for the supply medium; and/or the inlet for the cell broth is connected in a fluid conducting manner to a pump for the cell broth. With this pump (these pumps), supply medium and/or cell broth can be added in a controlled manner to the filter unit.

In principle, pumps suitable for the present invention include centrifugal pumps and/or positive displacement pumps, such as, for example, hose pumps, diaphragm pumps and piston pumps.

In accordance with an aspect of the present invention, at the inlets or, as the case may be, the outlets, which can be connected to a pump in a fluid conducting manner, it is possible to connect, instead of the pump, a pressurized container (for example, a bioreactor in the case of the inlet for the cell broth) or a generator of gravitational pressure to the inlet or, as the case may be, the outlet in a fluid conducting manner. As a result, the flow rate can also be initiated and controlled at the inlets and outlets.

In accordance with another of the preferred embodiments of the present invention, the outlet for the cell broth has a valve or a pump. The filtration pressure inside the retentate channel and, thus, the volume flow through the second filter medium can be adjusted with the valve and/or with the pump.

Furthermore, it is preferred that the outlet for the permeate has a valve. As a result, the permeate outlet can be closed. In accordance with another of the preferred embodiments of the present invention, the permeate outlet has a pump.

The amount of permeate liquid that is discharged can be regulated with the pump (and/or with the valve). In this case the amount that is discharged can be adjusted, for example, as a function of the target substance concentration or the contaminant concentration. Moreover, a pump, which is connected to the permeate outlet, can be used to generate a reversal of the permeate flow as a preferred intermediate step of the method of the present invention, as a result of which clogging of the filter medium can be counteracted; and a cover layer, which may have formed under certain circumstances, can be removed.

The first and second filter media are suitable for filtering the supply medium and the cell broth. The first and second filter media are at least partially permeable to the supply medium and the cell broth.

In accordance with a preferred embodiment, at least the second filter medium is not permeable to the cells contained in the cell broth. In this way and as a result of the direction of flow of the supply medium (see FIGS. 1 and 2), cells are prevented from passing from the retentate channel into the adjacent channels (permeate channel and supply channel). Preferably, the first filter medium is also not permeable to the cells contained in the cell broth.

In accordance with another of the preferred embodiments, the second filter medium is at least partially permeable to the cells and/or cell fragments contained in the cell broth. As a result, fractionation of the cells can be carried out with the filter unit of the bioreactor of the present invention. In this embodiment, too, the first filter medium is preferably not permeable to the cells contained in the cell broth.

The first filter medium and the second filter medium have in each case preferably a pore size of 0.001 µm to 1 mm, in particular, preferably 0.005 µm to 10 µm, independently of each other. In this context "independently of each other" means that the first and second filter media do not have to have the same pore size and/or material properties.

In accordance with an aspect of the invention, the pore size is determined using the capillary flow porometry for pore sizes of at least 0.1 µm (i.e., for microfiltration membranes having a mean pore size of 0.1 to 10 µm). In this context said capillary flow porometry is a gas/liquid porosimetry, in which the differential gas pressure levels and flow rates are measured via a membrane sample first in the moist state and then in the dry state. Before the measurement, the membrane sample is brought into contact with a wetting liquid so that all of the pores present are filled with this liquid. After filling the pores and introducing the sample, the measuring cell should be closed and the measurement started. The gas pressure is increased automatically and incrementally after the start of the measurement; and the pore diameters, corresponding to the applied pressure, are emptied by the gas pressure. This process is carried out until the relevant pore region has been detected, i.e., until even the smallest pores, present in the measuring region, are freed of the liquid. Thereafter, the pressure is lowered again; and the measurement on the sample, which is now dry, is automatically repeated. The difference between the two pressure/flow rate curves is used to calculate the pore size distribution using the Young Laplace equation (see also A. Shrestha, "Characterization of porous membranes via porometry", 2012, Mechanical Engineering Graduate Theses & Dissertations, Paper 38, University of Colorado at Boulder).

In order to determine pore sizes of more than 10 µm to 1 mm, the method, described in the Journal of Membrane Science 372 (2011), pages 66 to 74, and based on image analysis (image analysis), can be used.

In accordance with another aspect of the invention, the liquid-liquid displacement method is used for pore sizes of less than 0.1 µm. Said method has similarities with the capillary flow porometry. However, in this case it is not the gas flow rates, but rather the flow rates of the displacing liquid that are measured as a function of the differential pressure increase (see also R. Davila, "Characterization of ultra and nanofiltration commercial filters by liquid-liquid displacement porosimetry", 2013).

For the mixture, located in the retentate channel, the terms cell broth and retentate can be used interchangeably.

In accordance with a preferred embodiment of the invention, the first filter medium is a first filtration membrane. The second filter medium is preferably a second filtration membrane. It is particularly preferred that the first filter medium be a first filtration membrane and that the second filter medium be a second filtration membrane. The filtration membranes can be made, for example, of polyvinylidene fluoride, cellulose and derivatives thereof; polyether sulfone (PES) or polysulfone, where in this case special preference is given to the cross-linked cellulose hydrate.

If the filter unit is a flat filter module, then the inlet for the cell broth is attached preferably in a first edge region of the filter unit; and the outlet for the cell broth is attached in a second edge region of the filter unit, where said second edge region is opposite the first edge region. This arrangement defines a substantially uniform direction of flow of the cell broth from the inlet as a starting point to the outlet as an end point. For this reason the direction of flow of the cell broth is largely parallel to the flow path along the filter medium, i.e., in essence without deflections, as a result of which a stable and reliable flow of the cell broth through the filter unit can be ensured. In addition, the pressure drop in the filter unit as well as undesired effects of non-rectilinear flows on target substances, contained in the cell broth, and, in particular, on the cells can be minimized by the largely rectilinear flow path without deflections, loops or the like. For the above reasons it is also preferred that the inlet for the supply medium be attached in the first edge region of the filter unit.

In accordance with a preferred embodiment of the invention, the outlet for the permeate is attached in the second edge region of the filter unit. It is particularly preferred that at least one outlet for the permeate be attached in both the first edge region and the second edge region of the filter unit. In an additional embodiment of the invention, the outlets for the permeate are attached, as an alternative or in addition, in the third and/or fourth edge region of the filter unit. In a plan view of the filter unit from the side of the supply channel, the third edge region is located on the left side of the direction of flow. The fourth edge region is located correspondingly on the right side and, thus, lies opposite the third edge region. Owing to the projecting arrangement of the outlet(s), it is possible to achieve a particularly high permeate output and design advantages.

The first edge region encompasses preferably the outer third of the length of the filtration unit counter to the direction of flow. Correspondingly, the second edge region encompasses the outer third of the length of the filtration unit along the direction of flow. The same applies to the third and fourth edge regions. It is advantageous to design the first to fourth edge regions as small as possible. Therefore, the edge regions encompass, in particular, preferably the respective outer 20%, even more preferably the respective outer 10% and most preferably the respective outer 3%.

In principle, there is no special restriction with respect to the method of attaching the inlets and outlets. For example, the inlets and outlets can be attached so that the cell broth enters the retentate channel already in the direction of flow and leaves said retentate channel in the direction of flow. Correspondingly, the outlet for the permeate can be attached so that the permeate leaves the permeate channel in the direction of flow; and/or the inlet for the supply medium can be attached so that said supply medium enters the supply channel in the direction of flow. However, the inlets and outlets are attached preferably so that the supply medium enters the supply channel perpendicularly to the direction of flow; and then the cell broth enters the retentate channel perpendicularly to the direction of flow and leaves said retentate channel perpendicularly to the direction of flow. Such a method of attaching the inlets and outlets facilitates the arrangement of a plurality of filtration units to form a filter cartridge.

The filter unit has preferably a plurality of inlets for the cell broth, a plurality of outlets for the cell broth and a plurality of outlets for the permeate.

In accordance with an alternative embodiment, the filter unit is a flat filter module, wherein the inlet for the supply medium and the inlet for the cell broth are attached in a region in the center of the filter unit, so that the supply medium and/or the cell broth flows over the first and the second filter media in a direction that is moving away from the region in the center. In this embodiment the first and the second filter media are preferably disk shaped, so that the first and second filter media are used uniformly.

In a preferred embodiment the free volume of the supply channel and/or the retentate channel (space, dead volume or empty volume that is available for the supply medium and/or the cell broth) decreases in the direction of flow from the inlet for the cell broth to the outlet for the cell broth. Owing to the decreasing volume(s), the filter unit has a low pressure loss and a substantially deflection-free flow path of the supply medium and the cell broth. As a result, it is possible to increase the area performance of the filter unit and to operate the filter unit in the "single pass" mode (only a single pass-through of the cell broth takes place without recycling).

In another of the preferred embodiments of the invention, the decrease in the free volume along the direction of flow is achieved in that the width of the supply channel and/or the width of the retentate channel decreases/decrease in the direction of flow. The width runs along the first filter material and perpendicular to the direction of flow. In particular, preferably the width of the entire filter unit decreases in the direction of flow. The retentate channel, or the filter unit generally, is preferably trapezoidal in a plan view along a normal of the plane in which the first filter material is located. The basic trapezoidal shape of the supply channel and/or the retentate channel, or generally the filter unit, can be scalene, for example, right-angled, and is preferably isosceles.

In accordance with one embodiment, the height of the supply channel and/or the retentate channel, or generally the filter unit, can decrease in the direction of flow. For example, the supply channel and/or the retentate channel can be designed so as to be wedge shaped. The height of the supply channel and/or the retentate channel, or generally the filter unit, runs perpendicular to the first filter material and perpendicular to the direction of flow.

There is no particular restriction with regard to the width, length and height of the filter unit. The length runs parallel to the direction of flow and along the first filter material. The filter unit has a length of at least 50 mm, preferably at least 150 mm, more preferably 500 mm, and most preferably 750 mm or more.

In a preferred embodiment of the invention, the free volume of the permeate channel changes in the direction of flow. It is particularly preferred that the free volume of the permeate channel decrease in the direction of flow. As a result, it is possible to maintain, for example, the outer dimensions of the filter unit, which is designed preferably as a filtration cartridge.

The explanations for forming the retentate channel apply correspondingly to the permeate channel and vice versa.

"Free volume decreasing in the direction of flow" means that there is a cross sectional area $A_1$, through which the supply medium and/or the cell broth can flow and which lies in a plane, which has a normal that extends parallel to the direction of flow, and a corresponding cross sectional area $A_2$, which is parallel to $A_1$ and is farther away from the inlet for the supply medium and/or the cell broth than $A_1$, where in this case the surface area $A_1$, through which the supply medium and/or the cell broth can flow, is greater than $A_2$, and there are no correspondingly defined planes $A_1'$ and $A_2'$, for which the surface area of $A_1'$ is smaller than that of $A_2'$.

The decrease in the free volume can be constant ($A_1 \geq A_2$ holds for all $A_1$ and $A_2$) or continuous ($A_1 > A_2$ holds for all $A_1$ and $A_2$). It is also possible for the decrease in volume to be discontinuous; that means that a discontinuous drop or jump occurs in the cross sectional area along the direction of flow.

The change in the free volume of the retentate channel in the direction of flow is preferably in the range from 20 to 1 to 1.2 to 1, preferably at 10 to 1, depending on the filtration task. In this case the "change in the free volume of the retentate channel in the direction of flow" is to be understood to mean the ratio of the cross sectional area $A_1$ at the inlet for the cell broth to the cross sectional area $A_2$ at the outlet for the cell broth.

In one embodiment of the invention, the thickness of the supply channel and/or the thickness of the retentate channel and optionally the thickness of the permeate channel decreases/decrease in the direction of flow.

The supply channel, the retentate channel and the permeate channel are normally kept open by spacers. In a preferred embodiment of the invention, a flat spacer is mounted in the supply channel and/or in the retentate channel of the filter unit so that the free volume of the retentate channel decreases in the direction of flow.

Suitable spacers for filter units are known in the prior art and can be used in the supply channel, retentate channel and/or permeate channel of the filter unit of the bioreactor of the present invention. In accordance with an aspect of the invention, the spacers are modified preferably so that their volume increases in the direction of flow in order to achieve a decrease in volume of the free volume that is available for the supply medium and/or the cell broth. Preferred spacers may be textile materials made of organic or non-organic materials, such as woven fabrics, knitted fabrics, nonwovens or extruded meshes.

The spacer may be advantageously a nonplanar plate. The nonplanar plate may be a plate that has at least one nonplanar main surface. The main surfaces of a plate are the opposite surfaces with the largest surface area. The at least one nonplanar main surface can have irregularities in the form of a corrugated or serrated surface. In addition, the uneven surface can have protruding elements, such as cones (truncated cones), pyramids (truncated pyramids), nubs or other geometric figures. The nonplanar plate can also be in a corrugated or serrated form similar to a corrugated sheet, where in this case the corrugations or serrations extend preferably parallel to the direction of flow. Suitable materials for the nonplanar plate are the same as those listed below for spacers in the form of an open mesh matrix.

In accordance with a preferred embodiment, the spacer consists of an open mesh matrix or an extruded mesh. Spacers of this type are known in the prior art and have been described, for example, in the publication of the German patent application DE 100 22 259 $A_1$. As already mentioned above, the spacers are modified, according to an aspect of the present invention, preferably such that their volume increases in the direction of flow, in order to achieve a decrease in the volume of the free volume that is available for the supply medium and/or the cell broth. In principle, conventional spacers can also be installed in the filter unit of the present invention, for example, in the permeate channel and/or in the supply channel or in all of the channels of the filter unit with a width that decreases in the direction of flow.

As described above, a decreasing width can be achieved, for example, with a trapezoidal configuration of the channels or of the filter unit generally.

In one embodiment the mesh width of the open mesh matrix and/or of the extruded mesh can decrease in the direction of flow, in order to achieve a decrease in the free volume along the direction of flow. For instance, by way of example, the mesh width can be: 5/cm to 15/cm at the inlet for the supply medium and/or at the inlet for the cell broth; the mesh width can then be: 10/cm to 30/cm in the center between the respective supply-medium and/or cell-broth-medium inlets and the cell broth outlet; and the mesh width can then be 20/cm to 40/cm at the outlet for the cell broth.

As an alternative or in addition to the aforesaid, the open mesh matrix or, more generally, the extruded mesh can be constructed from intersecting longitudinal and transverse threads and can increase the number and/or thickness of the longitudinal and/or transverse threads in the direction of flow. The open mesh matrix consists preferably of an organic polymer, such as, for example, polypropylene, polyethylene, polyester, polyvinyl chloride or polyvinylidene fluoride or blends thereof. Furthermore, it is also possible for the open mesh matrix to be constructed from fibers of different types of polymers.

In another of the preferred embodiments of the invention, several layers of textile materials are arranged one above the other in the retentate channel such that the free channel volume decreases in the direction of flow. Such a decrease can be achieved, for example, by offsetting the layers, which are arranged one above the other, in the direction of flow. The layers, which are arranged one above the other, extend preferably as far as up to the second edge region. As a result, an increasing volume of the textile materials is taken up in the retentate channel in the direction of flow, so that the free volume decreases in the direction of flow. The textile materials, such as woven fabrics, knitted fabrics, nonwovens or extruded meshes, can be made of organic or non-organic materials.

The embodiments, which are illustrated here for achieving the decrease in the free volume of the supply channel or the retentate channel, can be combined with one another, as desired.

In accordance with an aspect of the invention, the retentate channel is delimited by a first filter material and a second filter material. The supply channel is delimited by at least one first filter material. The permeate channel is delimited by at least one second filter material. Adjacent to a retentate channel are a supply channel and a permeate channel. The filter unit of the bioreactor of the present invention consists preferably of a plurality of stacked arrangements comprised of supply channel, first filter material, retentate channel, second filter material, permeate channel, second filter material, retentate channel and first filter material, preferably closed off from a further supply channel, so that the stacked arrangements are combined to form a filter cartridge. Suitable embodiments for filter cartridges are known in the prior art. Preferably, each supply channel of these arrangements is delimited on both sides by a respective filter material, which corresponds to the first filter material, in order to segregate the supply channel from two adjoining retentate channels. Correspondingly, each permeate channel of these arrangements is delimited on both sides by a respective filter material, which corresponds to the second filter material, in order to segregate the permeate channel from two retentate channels. The first filter media and the second filter media can be different from one another. This means that, in principle, different types of first filter media and different types of second filter media can be used. Preferably the same type of first filter media and/or the same type of second filter media are used.

In accordance with a preferred embodiment, the first and second filter media have, independently of one another, a substantially uniform thickness of preferably 50 μm to 10,000 μm, in particular, preferably 150 μm to 1,000 μm. If the delimiting of the supply channel by the first filter material and the further delimiting of the supply channel and/or the delimiting of the retentate channel by the first and second filter material do not run parallel to one another, then the free volume of the supply channel and/or the retentate channel can be designed so as to be wedge shaped, so that the free volume decreases in the direction of flow. It is particularly preferred that the supply channel, the retentate channel and the permeate channel be delimited on both sides by substantially parallel surfaces.

The shape of the filter unit of the bioreactor of the present invention is not subject to any particular restriction. The filter unit may be, for example, cuboid or cylindrical.

In a further aspect the present invention relates to a method for treating a cell broth, said method comprising the steps of (A) providing a filter unit, wherein the filter unit comprises at least one supply channel, at least one first filter medium, at least one retentate channel, at least one second filter medium and at least one permeate channel, arranged so that the first filter medium segregates the supply channel and the retentate channel from one another; and the second filter medium segregates the retentate channel and the permeate channel from one another, wherein the supply channel is connected in a fluid conducting manner to at least one inlet for a supply medium; the retentate channel is connected in a fluid conducting manner to at least one inlet for the cell broth and to at least one outlet for the cell broth; the permeate channel is connected in a fluid conducting manner to at least one outlet for a permeate; (B) feeding the supply medium into the inlet for the supply medium; (C) feeding the cell broth into the inlet for the cell broth; (D) discharging the cell broth from the outlet for the cell broth; and (E) discharging the permeate from the outlet for the permeate.

The explanations with respect to the bioreactor, the filter unit thereof and the method for treating a cell broth are mutually applicable to one another.

The supply medium is not subject to any particular restriction and may be a fluid or a suspension. The supply medium contains preferably water and optionally a gaseous fluid. Examples of gaseous fluids, which are suitable according to the invention, are oxygen, nitrogen, air and noble gases, such as argon. It is particularly preferred that the supply medium be an aqueous suspension or an aqueous solution. Specific exemplary embodiments of the supply medium are aqueous culture media (nutrient solutions), buffer solutions (for washing), and water (which can be optionally demineralized or distilled).

In accordance with a preferred embodiment, the treatment of the cell broth comprises washing the cells, adding or exchanging a culture medium, changing the concentration of the cells in the cell broth, fractionating the cells and/or gassing the cells.

It is particularly preferred that the treatment be a washing procedure of the cells (cell washing). "Cell washing" means in the context of the present invention that at least one component of the cell broth, apart from the cells, is removed at least partially from the cell broth. For example, when washing cells, a cell broth, which contains a culture medium and (biological) cells as well as metabolic products of the cells and/or impurities, can be freed at least partially of the metabolic products and/or the impurities. In so doing, the culture medium of the cell broth, supplied in step (C), is replaced at least partially by the supply medium. The metabolic products of the cells and/or the impurities leave the filter unit as constituents of the permeate. In the event that the cell treatment is a cell washing procedure, the supply medium is preferably a washing fluid, such as, for example, a washing buffer solution (for example, a saline solution), a stabilizing buffer solution (for example, sodium phosphate buffer, citrate buffer, acetate buffer) or (optionally demineralized or distilled) water. In the case of the cell washing procedure, however, the supply medium can also be a nutrient medium.

In accordance with an aspect of the invention, the metabolic products include both undesired and/or unnecessary metabolic products and desired metabolic products produced by the cells. A desired metabolic product of the cells may be, for example, a pharmaceutical active ingredient.

In accordance with a preferred embodiment, in step (A) the above described bioreactor of the present invention is provided with a filter unit; in step (C) the cell broth is fed from the interior of the bioreactor into the inlet for the cell broth; and in step (D) the cell broth is discharged from the outlet for the cell broth into the interior of the bioreactor. This embodiment of the present invention makes it possible to operate continuously a method which makes use of cells and in which a cell treatment is required.

By adjusting the ratio of the volume flow of the supply medium, supplied in step (B), to the volume flow of the cell broth, supplied in step (C), the ratio of the number of cells in the permeate to the number of cells remaining in the cell broth can be adjusted (degree of separation) in the case of cell fractionation at a constant volume flow at the outlet for the cell broth.

In the case of a cell washing procedure, the above volume flow ratio can be used to adjust the exchange ratio of the cell broth (volume fraction of the supplied cell broth that is replaced by the supply medium). The ratio of the volume flow of the supply medium, supplied in step (B), to the volume flow of the cell broth, supplied in step (C), is preferably 1:10 to 10:1.

By adjusting the ratio of the volume flow of the cell broth, supplied in step (C), to the volume flow of the cell broth, discharged in step (D), the concentration of the cells in the discharged cell broth can be adjusted. In this way the method of the present invention makes it possible to decrease and also to increase the cell concentration in the discharged cell broth. In accordance with a preferred embodiment, the ratio of the volume flow of the cell broth, supplied in step (C), to the volume flow of the cell broth, discharged in step (D), is 1:10 to 10:1.

If the method of the present invention for the treatment of a cell broth includes an increase of the concentration of the cells in the cell broth, then the concentration of the cell broth discharged in step (D) is preferably 2 to 10 times the concentration of the cell broth supplied in step (C).

In a preferred embodiment the method of the present invention further comprises the step (C') of feeding the cell broth into the outlet for the cell broth and the step (D') of discharging the cell broth from the inlet for the cell broth. This flow reversal can be carried out, for example, by one or two pumps, connected in a fluid conducting manner to the inlet for the cell broth and/or the outlet for the cell broth. The reversal of the direction of flow with the preferred steps (C') and (D') (see, for example, FIG. 1, direction of flow from 8 to 7, instead of the direction of flow from 7 to 8, indicated by an arrow) can lead advantageously to the removal of a cover layer, which may have been formed under certain circumstances on the second filter medium (5) or the first filter medium. As a result, it is possible either to prevent the second filter medium (5) from being clogged; or to reverse such a clogging of said first or second filter medium. A reversal can be repeated, as required. This means that the steps (C') and (D') can be repeated.

Moreover, a pump, which is connected to the permeate outlet, can be used to generate a reversal of the permeate flow and, in so doing, also a reversal of the flow through the second filter medium (5) as a preferred intermediate step of the method of the present invention. As a result, such a reversal can also have a counter effect on the clogging of the second filter medium (5) and can remove a cover layer, which may have formed on said second filter medium under certain circumstances.

In accordance with a preferred embodiment of the method of the present invention, various supply media can be supplied at different times in step (B). That means that the composition of the supply medium, supplied in step (B), can vary over time. Therefore, it is possible, for example, to switch between a washing buffer and a culture medium (nutrient solution). This means that a first supply medium (for example, a fresh culture medium) can be added in a first phase of the method of the present invention; and a second supply medium (for example, a washing buffer) can be added in a second phase, where in this case the first and second phases can alternate, if necessary. If a culture medium is added as a supply medium in one of the two phases, then the outlet for the permeate is preferably closed, so that the added culture medium is not lost. As soon as a washing buffer is added again as a supply medium, the permeate channel can be opened again for purposes of cell washing.

In a preferred embodiment of the method, the supply medium is supplied at a pressure of 0.1 to 4 bar. It is particularly preferred that the supply medium be supplied at a pressure that is greater than the retentate outlet pressure.

Furthermore, the pressure between the retentate channel and the permeate channel is preferably 0.1 to 1.5 bar.

The method of the present invention is operated preferably in a continuous mode, that is to say, with constant/continuous addition of the supply medium and the cell broth, as a result of which a particularly efficient and economical method for treating a cell broth can be provided. In accordance with an aspect of the invention, a "continuous" method for treating a cell broth is to be understood to mean a method, in which both the supply medium and the cell broth are added continuously.

In a preferred embodiment of the method, several filter units, which are independent of one another, are provided in step (A) and are connected in series so that the outlet for the cell broth of the respective upstream filter unit is connected in a fluid conducting manner to the inlet for the cell broth of a downstream filter unit. In addition, in step (C) the cell broth in this embodiment is fed into the inlet for the cell broth of that filter unit, upstream of which no other filter unit is connected (first filter unit); and in step (D) the cell broth is discharged from the outlet for the cell broth of that filter unit, downstream of which no other filter unit is connected (last filter unit). As a result, the cell broth passes through the filter units, which are connected in series, from the first to the last. Preferably 2 to 10, in particular, preferably 2 to 5 filter units are connected in series. In this embodiment the supply medium is fed to each of the filter units connected in series. Although it is possible to use different types of supply media, it is preferred to feed the same supply medium to each of the filter units. Each of the filter units, which are connected in series, as described above, is preferably in the form of a filter cartridge.

In a preferred embodiment of the method, a plurality of filter units, which are disclosed in the present invention and are independent of one another, are provided and connected in parallel in step (A). Parallel and series connections can be combined with one another.

In another of the preferred embodiments of the method, the retentate (cell broth), discharged in step (D), is at least partially fed back directly into the inlet for the cell broth. If a single pass through the filter unit is not sufficient, then it is possible to use a closed loop process to achieve an improved result of the method. In this context the addition of the supply medium and the removal of the permeate take place without recycling. If several filter units are connected in series, then, in principle, any retentate stream can be fed back to each inlet for the cell broth. In so doing, the cell broth of each individual filter unit is fed back preferably to the inlet for the cell broth of the same filter unit.

The method of the present invention is operated preferably under the following conditions:

$$P_{EVK} \geq P_{ER};$$

$$x = V_{EVK}/V_{ER},$$

preferably x≥1, in particular, preferably 3≤x≤10; and $$k = V_{ER}/V_{AR},$$

preferably k≥1;
where
$P_{EVK}$ is the pressure, at which the supply medium is added,
$P_{ER}$ is the retentate inlet pressure, i.e., the pressure, at which the cell broth is added to the filtration device,
$V_{AR}$ is the volume flow of the discharged cell broth,
$V_{EVK}$ is the volume flow of the supply medium,
$V_{ER}$ is the volume flow of the supplied cell broth,
x is the so-called exchange ratio, and
k is the so-called concentration factor.

Figure 6:
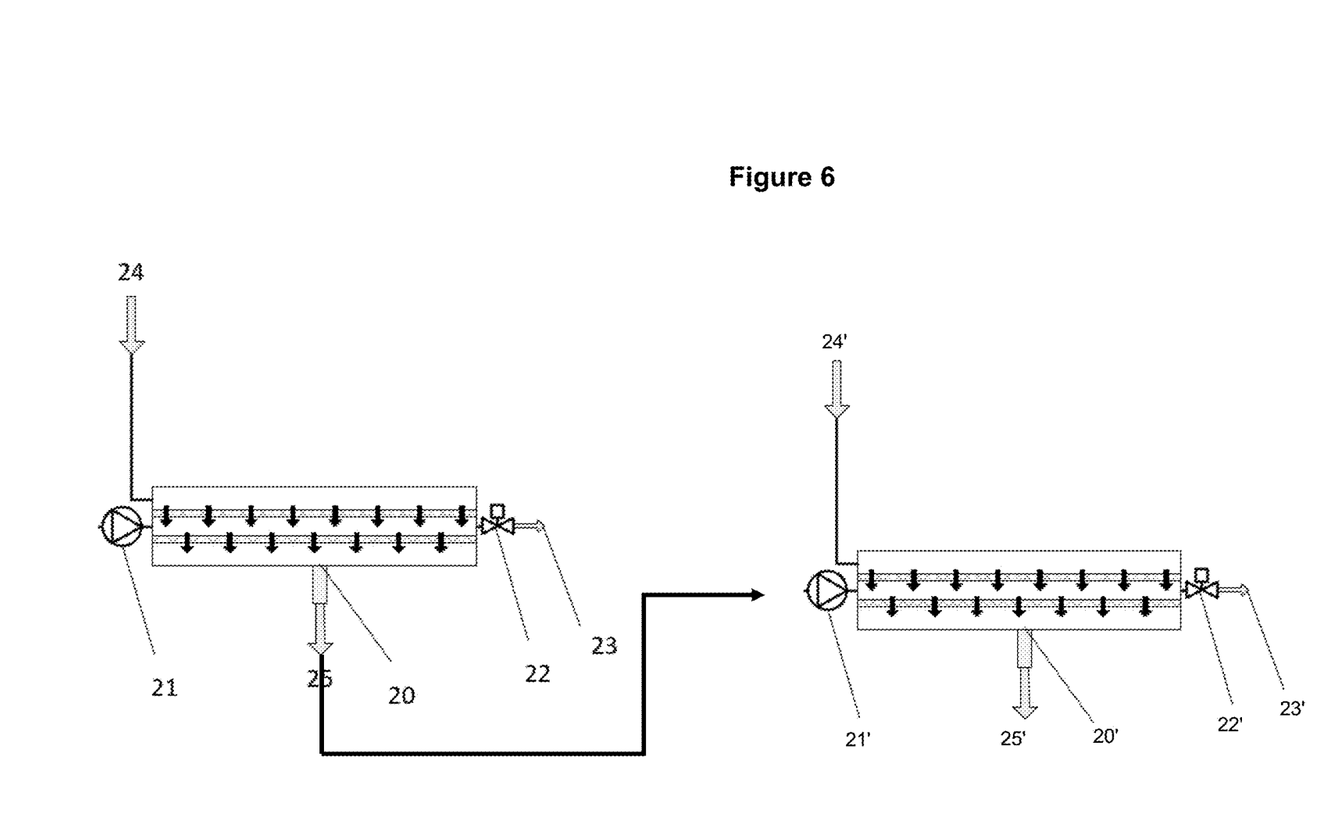
FIG. 6 shows an exemplary embodiment of the present invention, in which a further filter unit is connected in a fluid conducting manner to a first filter unit by way of a permeate outlet.

In accordance with a preferred embodiment of the present invention, at least one further filter unit (20') is connected in a fluid conducting manner to the aforementioned filter unit (13, 20) by way of the permeate outlet (25) (see FIG. 6). Otherwise, the embodiments with respect to the filter unit (13, 20) apply mutatis mutandis to the at least one further filter unit (20').

The permeate (36), which is discharged in step (E) in the method of the present invention, can be worked up in the at least one further filter unit (20'). The at least one further filter unit (20') is operated in the same manner as is the filter unit (13, 20). In this context it is particularly preferred to select, for the filter media which are used for the at least one further filter unit (20'), a pore size, at which one or more target substances (product), which is/are contained in the permeate (36) from the filter unit (13, 20), is/are conveyed from the inlet for the retentate of the at least one further filter unit (20') [where the inlet of 20' corresponds to the inlet (7) for the cell broth of the filter unit (13, 20)] through the retentate channel to the outlet for the retentate (23') of the at least one further filter unit (20') [where the outlet of 20' corresponds to the outlet (8, 15, 23) for the cell broth of the filter unit (13, 20)]. This means that the at least one target substance remains preferably in the retentate of the filter unit (20'). The supply channel of the at least one further filter unit (20') is connected in a fluid conducting manner to at least one inlet for a further supply medium. In this case a buffer solution is used preferably as the supply medium. The at least one further filter unit (20') can be used, in particular, to remove/isolate the residual components (for example, residues of a culture medium) from the permeate (36) from the first filter unit (13, 20).

BRIEF DESCRIPTION OF THE DRAWINGS

FIGS. 1 and 2 show exemplary embodiments of the present invention, wherein

FIGS. 3 and 4 show exemplary embodiments of the present invention, wherein

DETAILED DESCRIPTION

FIGS. 1 to 4 show in schematic form exemplary embodiments of a method according to the present invention for treating a cell broth as well as a (filter unit of an) exemplary embodiment of the bioreactor according to the present invention, wherein the flow patterns of materials and the flow directions are indicated by arrows.

Figure 1:
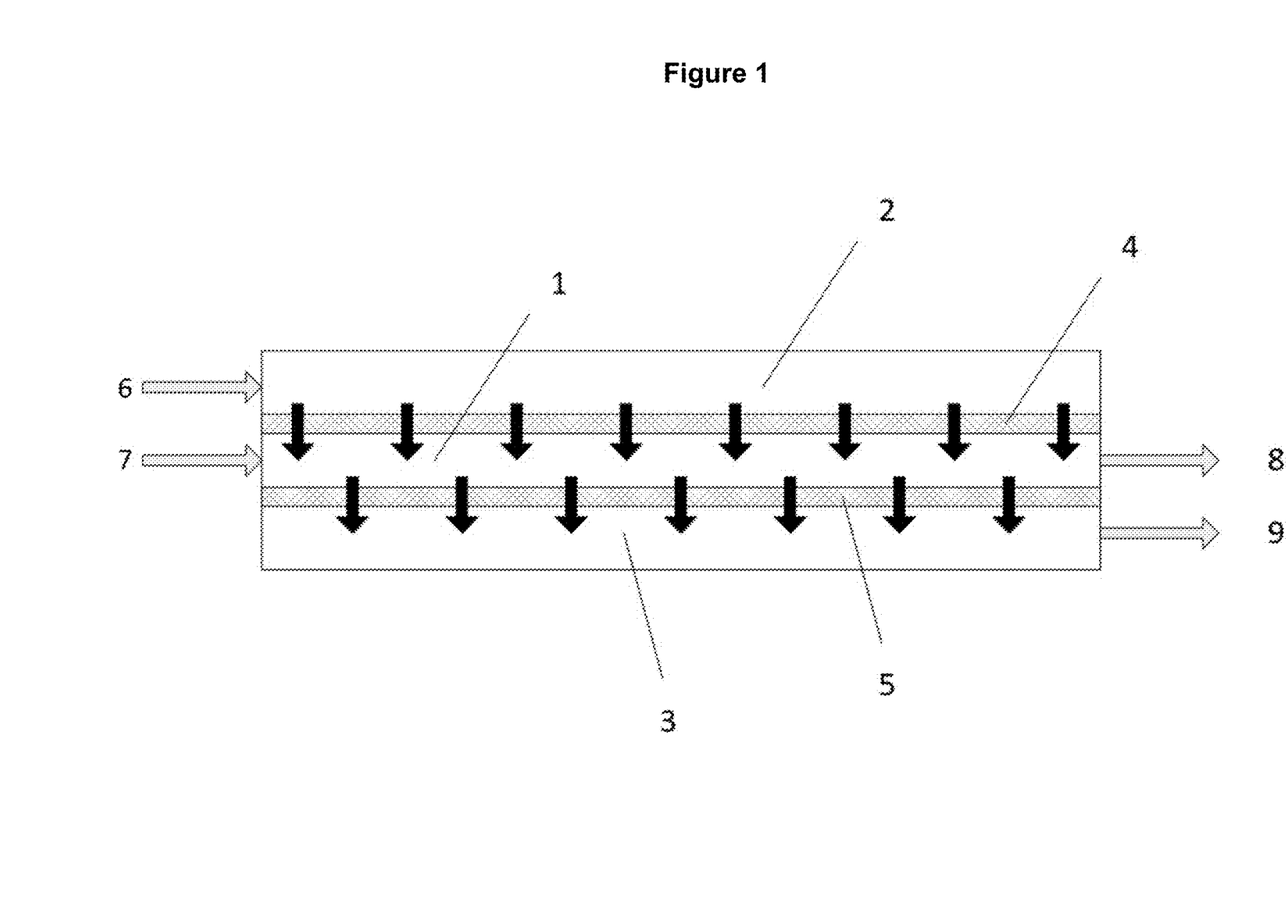
FIG. 1 shows a filter unit for treating a cell broth.
Figure 2:
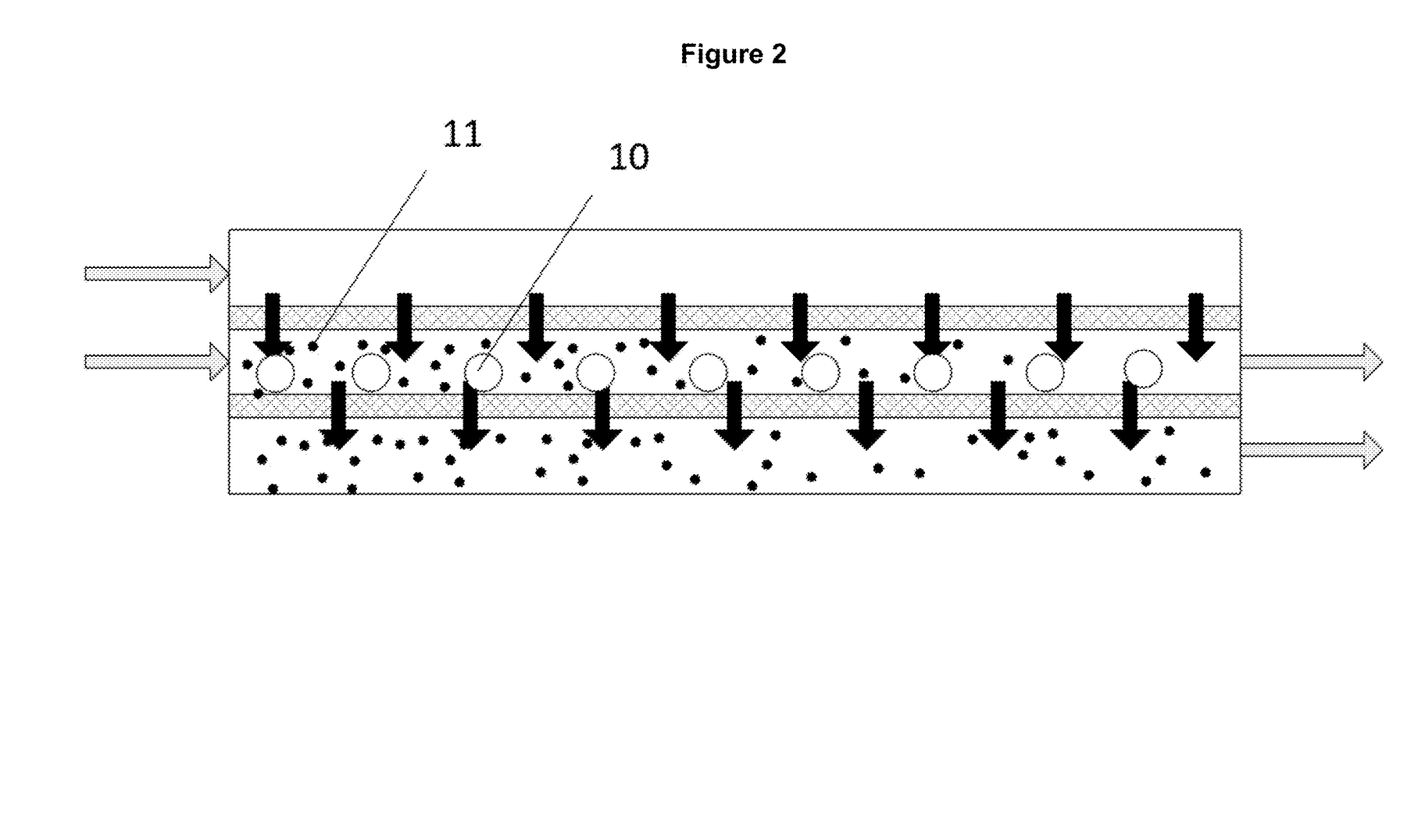
FIG. 2 shows a filter unit that permits some cell broth impurities to pass.

FIGS. 1 and 2 show filter units as well as methods for the treatment of a cell broth in exemplary experimental setups. The second filter medium (5) in FIG. 2 retains the cells (10) and allows impurities (11) to pass through, so that the cell broth leaves the retentate channel (1) in a cleaned state. The cell broth is fed into the filter unit by way of the inlet (7) to the retentate channel (1). A fluid (liquid/gas) is pumped into the filter unit by way of the inlet (6) to the supply channel (2). The fluid (supply medium) is introduced into the retentate channel (1) by way of a pressure gradient; and at the same time a filtration takes place in the permeate channel (3) by way of the pressure gradient between the retentate channel (1) and the permeate channel (3). The pressure gradient can be controlled, for example, with a valve and/or a pump at the outlet (8) of the retentate channel. The cells (10) are retained by selecting a suitable separation limit of the second filter medium and do not pass through the second filter medium. Smaller molecules, such as proteins, on the other hand, pass through the filter medium. The same also applies to the culture medium (supply medium). Smaller components (constituents of the cell broth and the supply medium that can pass through the second filter material) are discharged through the permeate outlet (9). As a result, the concentration of smaller components in the cell broth/in the retentate decreases accordingly in the direction of the retentate outlet (8).

Figure 3:
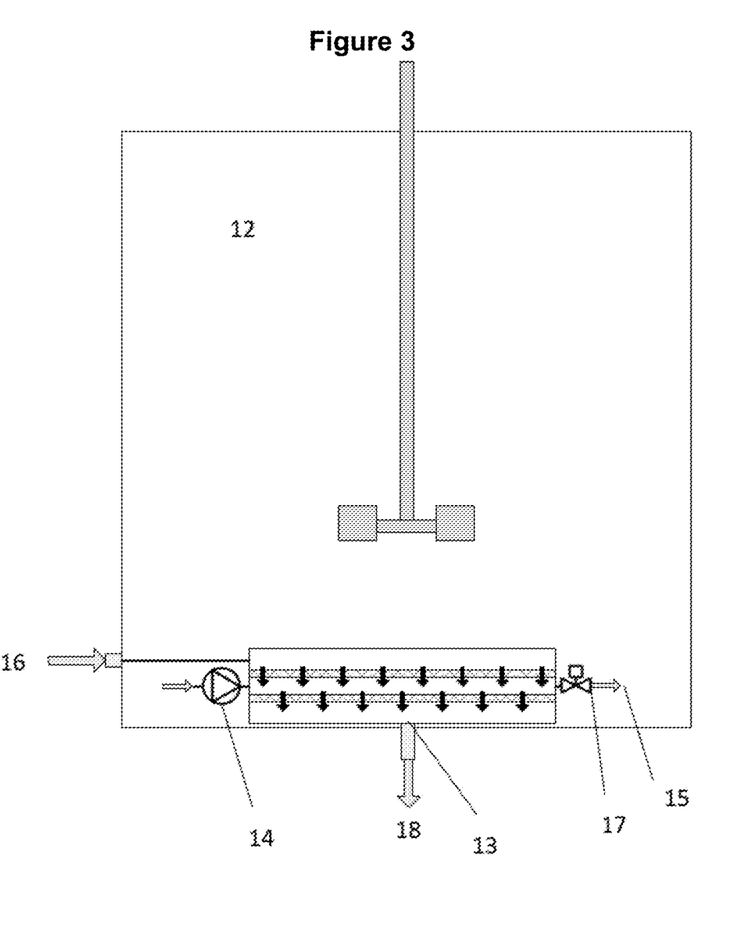
FIG. 3 shows a filter unit located inside a bioreactor.
Figure 4:
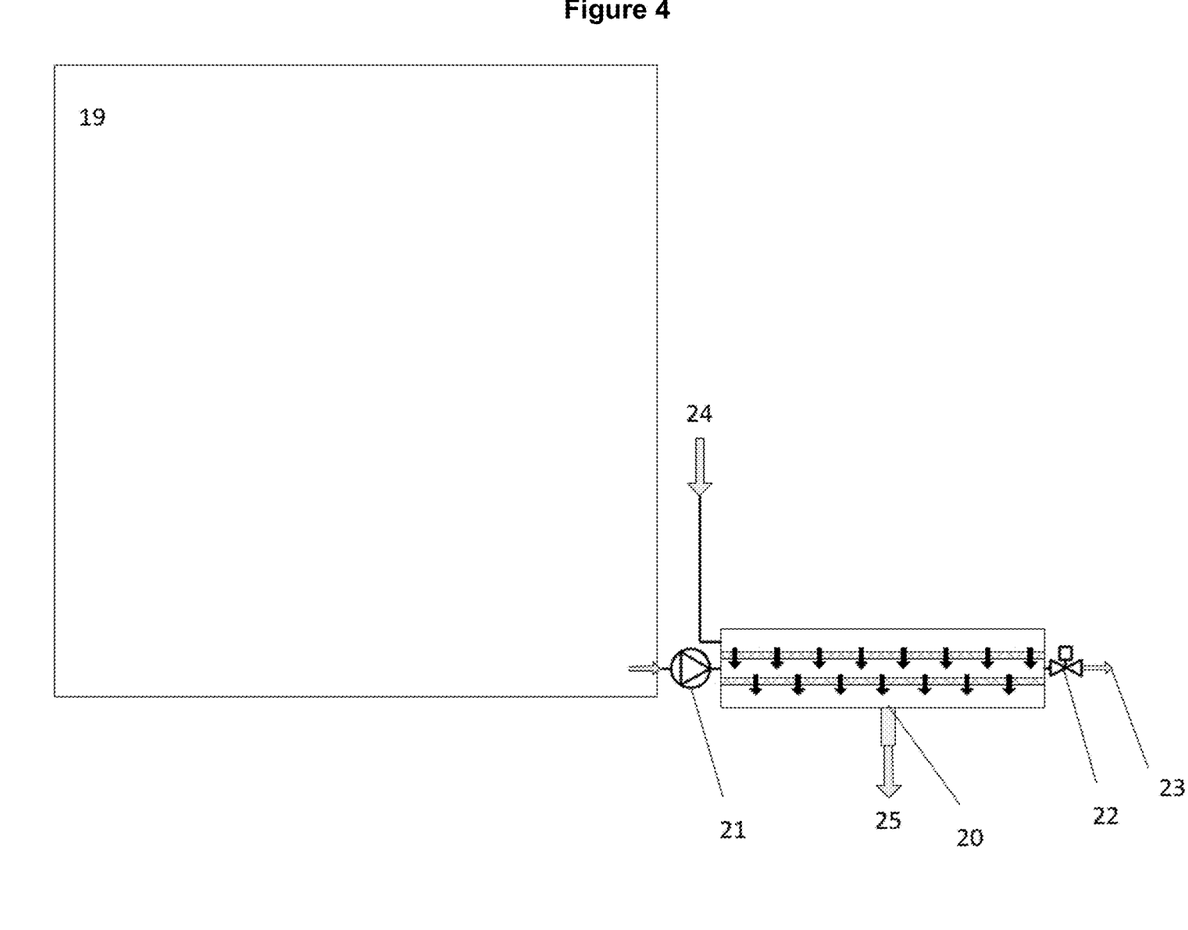
FIG. 4 shows a filter unit located outside a bioreactor.

Further exemplary embodiments of the present invention are shown in FIGS. 3 and 4 and will be explained in the following. In the embodiment of FIG. 3, the filter unit (13) is located inside the interior of the bioreactor (12). In the case of an arrangement of the filter unit in the interior of the bioreactor, the bioreactor has preferably an outer connection (16) for the supply medium. Supply medium can be supplied to the supply channel from the outside by way of the connection (16). In the embodiment of FIG. 4, the filter unit (20) is located outside the interior of a tank (19).

Filter Unit, Integrated in a Bioreactor for Obtaining Monoclonal Antibodies and Culture Medium Exchange This embodiment is illustrated in FIG. 3.

The filter unit (13) is integrated in a bioreactor (12) (for example, in a perfusion bioreactor for producing a monoclonal antibody (=product) using ovarian cells of the Chinese dwarf hamster). The cell broth (34, 40) in the bioreactor (12) is fed by a pump (14) into the retentate channel (1) of the filter unit (13) and leaves the retentate channel again directly into the perfusion bioreactor (12) by way of the retentate outlet (15). In so doing, the cells (10) pass only through the retentate channel (1) without passing into the supply (2) or permeate channel (3). The product and the contaminants pass through the filter medium (4) into the permeate channel (3).

Culture medium and/or washing buffer is/are optionally fed through a connection (16) to the perfusion bioreactor. The procedure also makes it possible to change the supplied media in different phases by way of the connection (16). Optionally the permeate outlet (18) can be closed, for example, in the phase of supplying fresh culture medium. In an additional phase the permeate outlet (18) is opened again; and washing buffer is supplied.

The filtration pressure is adjusted by using a valve (17) or a pump (not shown in FIG. 3) at the outlet (15) of the retentate channel. Product and contaminants (by-products, cell constituents, etc.) are discharged through the permeate outlet (18) for further work-up.

Method for Concentrating and for Washing a Cell Broth

This embodiment is shown in FIG. 4.

The retentate channel (1) of the filter unit (20) is connected to a tank (19), which contains a cell broth, through a pump (21). The cell broth from the tank (19) is fed to the retentate channel (1) of the filter unit (20). The filtration pressure is adjusted by through a valve (22) or a pump (not shown in FIG. 4) at the outlet of the retentate channel (23), and the volume flow at the outlet (23) is regulated in relation to the inlet volume flow. A solution is fed as a supply medium (38) through the connection (24) to the supply channel (2). Contaminants as well as the major portion of the solution are discharged through the permeate outlet (25). Cells (10) in the retentate can be fed through the retentate outlet (23) and then, as the case may be, to the next step or to a further tank or back to the original tank (19). The cell broth is concentrated by a factor of preferably 2 to 10.

The present invention is explained through the following example, but is not limited thereto.

EXAMPLE

Cell Washing of a Yeast Cell Suspension with Bovine Serum Albumin as the Product The underlying test setup is shown in FIGS. 1 and 2. A membrane, made of PES and having a pore size of 0.1 μm, was used as the first (4) and second (5) filter medium. The membrane area was 0.216 m$^2$ in each case. A cell broth (30 g/l of baker's yeast, 10.6 g/l of bovine serum albumin (protein) and 0.9% NaCl solution in water) was introduced into the inlet (7). Tap water was fed as a supply medium into the supply channel (2). The protein concentration and mass of the respective total volume of the cell broth before and after the washing as well as the protein concentration and mass of the permeate were determined. The results are shown in Tables 1 and 2.

TABLE 1

| t [min] | $P_{ER}$ [bar] | $V_{AR}$ [ml/min] | $V_{AP}$ [ml/min] | $V_{EVK}$ [ml/min] | $V_{ER}$ [ml/min] | $V_{ER}:V_{AR}$ [—] | $V_{EVK}:V_{ER}$ [—] |
|---|---|---|---|---|---|---|---|
| 5 | 0.12 | 64 | 64 | 61 | 64 | 1.0 | 1.0 |
| 12 | 0.13 | 66 | 66 | 62 | 65 | 1.0 | 1.0 |
| 20 | 0.17 | 66 | 66 | 71 | 62 | 0.9 | 0.9 |
| 30 | 0.24 | 66 | 66 | 61 | 69 | 1.0 | 1.1 |
| 50 | 0.37 | 66 | 64 | 61 | 68 | 1.0 | 1.1 | t time of measurement
$P_{ER}$ pressure, at which the cell broth was added
$V_{AR}$ volume flow at the outlet of the retentate channel
$V_{AP}$ volume flow at the outlet of the permeate channel
$V_{EVK}$ volume flow at the inlet of the supply channel
$V_{ER}$ volume flow at the inlet of the retentate channel

TABLE 2

|  | Conductivity [mS/cm] | Volume [l] | Mass Concentration (Protein) [g/l] | Mass (Protein) [g] |
|---|---|---|---|---|
| Cell broth before washing | 14.55 | 5 | 10.6 | 53.0 |
| Permeate | 10.52 | 5.1 | 6.72 | 34.3 |
| Cell broth after washing | 3.93 | 4.95 | 3.1 | 15.3 |

The result shows a decrease in the NaCl and protein concentration in the cell suspension (retentate).

Figure 5:
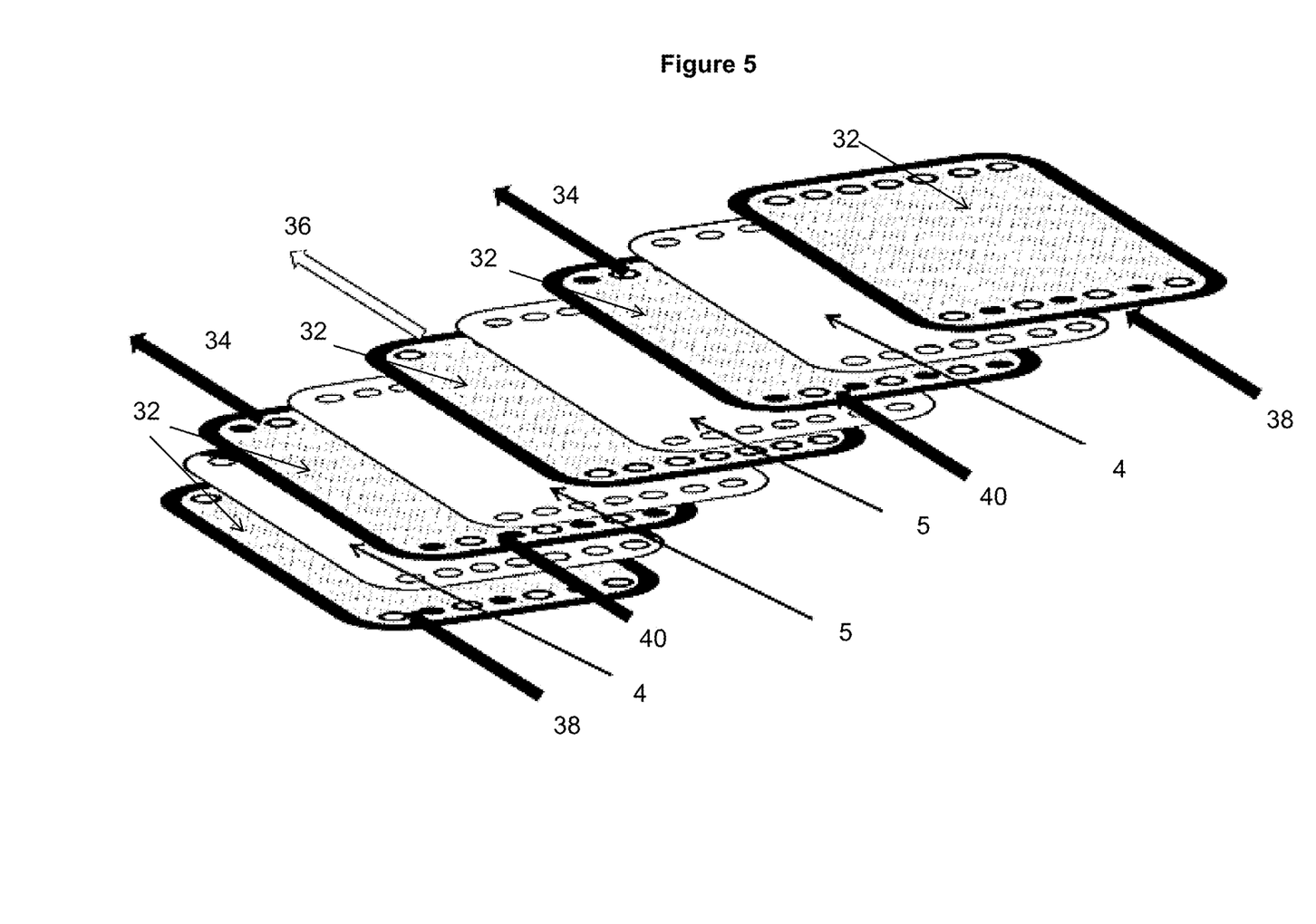
FIG. 5 shows an exploded view of one possible design of a filter unit.

FIG. 5 shows an exploded view of one possible design of a filter unit, which is suitable for the bioreactor (12) of the present invention and for the method of the present invention, with a flat first filter medium (4) and a flat second filter medium (5), where in this case the flow patterns of the supply medium (38), the cell broth (34, 40) and the permeate (36) are illustrated by arrows. The supply channel (2), the retentate channel (1) and the permeate channel (3) are kept open by spacers (32) for the supply medium (38), the cell broth (34, 40) or, as the case may be, the permeate (36). In the exploded drawing of FIG. 5, the components of the filter unit are offset from one another, in order to provide greater clarity. In reality, the components/layers of this embodiment are arranged one above the other such that the holes (passage openings) in the edge regions form channels.

FIG. 6 shows a further exemplary embodiment of the present invention, wherein at least one further filter unit (20') is connected in a fluid conducting manner to the filter unit (20) by way of the permeate outlet (25).

LIST OF REFERENCE NUMERALS 1 retentate channel
2 supply channel
3 permeate channel
4 first filter medium
5 second filter medium
6 inlet for supply medium
7 inlet for cell broth
8, 15, 23, (23') outlet for cell broth (or outlet for retentate)
9, 18, 25, 25' outlet for permeate
10 cells
11 impurities
12 (perfusion) bioreactor
13, 20, 20' filter unit
14, 21, 21' pump
16 connection to inlet for supply medium
17, 22, 22' valve
19 tank
24, 24' connection for supply medium
32 spacer
34, 40 cell broth
36 permeate
38 supply medium

What is claimed is:

1. Bioreactor with a filter unit, wherein
the bioreactor defines an interior, and
the filter unit comprises
   at least one supply channel,
   at least one first filter medium,
   at least one retentate channel,
   at least one second filter medium,
   at least one permeate channel,
   a further second filter medium,
   a further retentate channel, and
   a further first filter medium,
arranged such that
   the first filter medium delimits the supply channel and the retentate channel from one another,
   the second filter medium delimits the retentate channel and the permeate channel from one another,
   the further second filter medium delimits the permeate channel and the further retentate channel from one another, and
   the further first filter medium delimits the further retentate channel,
wherein
the supply channel is connected in a fluid conducting manner to at least one inlet for a supply medium and is connected in a fluid permeable manner via the first filter medium to the retentate channel,
the retentate channel is connected in a fluid conducting manner to at least one inlet for a cell broth and to at least one outlet for the cell broth and is connected in a fluid permeable manner via the second filter medium to the permeate channel,
the permeate channel is connected in a fluid conducting manner to at least one outlet for a permeate,
the interior of the bioreactor is connected in a fluid conducting manner to the inlet for the cell broth and in a fluid conducting manner to the outlet for the cell broth, and
the supply channel, the one first filter medium, the one retentate channel, the one second filter medium, the further second filter medium, the further retentate channel, and the further first filter medium form a stacked arrangement forming a filter cartridge.

2. Bioreactor as claimed in claim 1,
wherein the filter unit is arranged inside the interior.

3. Bioreactor as claimed in claim 1,
wherein the filter unit is arranged outside the interior.

4. Bioreactor as claimed in claim 1,
wherein the filter unit is a flat filter module, spiral wound fiber module or hollow fiber module.

5. Bioreactor as claimed in claim 1,
wherein the inlet for the supply medium is connected in a fluid conducting manner to a pump for the supply medium.

6. Bioreactor as claimed in claim 1,
wherein the inlet for the cell broth is connected in a fluid conducting manner to a pump for the cell broth.

7. Bioreactor as claimed in claim 1,
wherein the outlet for the cell broth and/or the outlet for the permeate comprises a valve.

8. Bioreactor as claimed in claim 1,
wherein the outlet for the cell broth comprises a pump.

9. Bioreactor as claimed in claim 1,
wherein the outlet for the permeate comprises a bidirectional pump.

10. Bioreactor as claimed in claim 1, wherein the supply channel is connected via the first filter medium to the retentate channel with a first pressure gradient.

11. Bioreactor as claimed in claim 10, wherein the retentate channel is connected via the second filter medium to the permeate channel with a second pressure gradient controlled with a pump and/or a valve connected in a fluid conducting manner to the retentate channel.

12. Bioreactor as claimed in claim 1, wherein the retentate channel is connected via the second filter medium to the permeate channel with a second pressure gradient controlled with a pump and/or a valve connected in a fluid conducting manner to the retentate channel.

\* \* \* \* \*